United States Patent [19]
Krasnov

[11] 3,986,214
[45] Oct. 19, 1976

[54] SURGICAL METHOD OF FIXATION OF ARTIFICIAL EYE LENSES

[76] Inventor: Mikhail Mikhailovich Krasnov, ulitsa Vesnina, 30, kv. 12, Moscow, U.S.S.R.

[22] Filed: Nov. 26, 1975

[21] Appl. No.: 635,338

[52] U.S. Cl. .................................. 3/13; 128/303.1
[51] Int. Cl.² ................. A61F 1/16; A61F 1/24; A61B 17/36
[58] Field of Search ................ 3/13, 1; 128/303.1, 128/334 R, 303 R

[56] References Cited
UNITED STATES PATENTS

| | | |
|---|---|---|
| 3,673,616 | 7/1972 | Federov et al. ........................ 3/13 |
| 3,865,113 | 2/1975 | Sharon et al. ..................... 128/303.1 |
| 3,906,551 | 9/1975 | Otter ....................................... 3/13 |
| 3,910,276 | 10/1975 | Polanyi et al. .................. 128/303.1 |

OTHER PUBLICATIONS

"History of Intraocular Implants" by D. P. Choyce, Annals of Ophthalmology, Oct. 1973, pp. 1113–1120, 3–13.

Primary Examiner—Ronald L. Frinks
Attorney, Agent, or Firm—Steinberg and Blake

[57] ABSTRACT

A surgical method of fixation of artificial eye lenses formed as an optic lens with supporting members intended for being passed through apertures in the periradicular zone of the iris, which comprises perforating apertures for said supporting members by means of a focused laser beam, incising the anterior chamber of the eye, removing the opacified eye lens, implanting an artificial lens, and applying surgical sutures.

3 Claims, 15 Drawing Figures

SURGICAL METHOD OF FIXATION OF ARTIFICIAL EYE LENSES

The present invention relates to ophthalmology, and more specifically, to a method of fixation of artificial eye lenses used for correcting optic defects in aphacia and restoring binocular vision, said devices being formed as an optic lens with appliances for the fixation thereof to the periradicular zone of the iris, and said appliances comprising two or three supporting members with a step-like bend intended for being inserted through apertures in the periradicular zone of the iris, or member and a loop for suturing the optic lens to the iris.

There is known a surgical method of fixation of artificial eye lenses formed as an optic lens with a means for fixation thereof to the periradicular zone of the iris that is provided with a supporting member. The said method consists in that, prior to incising the eyeball with a knife-needle, one, two or three apertures are perforated in the periradicular zone of the iris in accordance with the number of supporting members of the artificial eye lens used. Following this stage, the anterior chamber of the eye is incised. The artificial eye lens is introduced into the chamber and fixed by the supporting members in the apertures preformed in the periradicular zone of the iris, either prior to or following cataract extraction.

In case the supporting portion of the artificial eye lens is formed as one supporting member and a loop for suturing, the latter being located on the side of the optic lens contralateral to the supporting member, the optic lens is sutured to the periradicular zone of the iris following the fixation of the supporting member in the aperture preformed in the iris.

However, the making of the apertures for the supporting members in accordance with the prior art method of fixation of artificial eye lenses requires a high level of skill on the part of the surgeon, and may result in such complications as injuries of the eye lens capsule or of the corneal endothelium. Haemorrhages from the iris may also be caused during the dissection of the iris tissue.

It is an object of the present invention to provide a surgical method of fixation of artificial eye lenses that would simplify the surgical procedure.

It is another object of the invention to provide a surgical method of fixation of artificial eye lenses that would minimize the possible risk of complications developing during the perforation of apertures in the iris for the supporting members of the artificial eye lens.

It is a further object of the invention to provide a surgical method that would permit forming apertures in the iris, of a required diameter wherethrough the supporting members of the artificial eye lenses are to be inserted.

The foregoing objects are attained by that in a surgical method of fixation of artificial eye lenses formed as an optic lens with supporting members, which comprises making apertures in the periradicular zone of the iris wherethrough said supporting members are to be inserted incising the eyeball cavity, extracting the cataract, implanting an artificial eye lens, fixing the supporting members thereof in said apertures and applying sutures to the incisions, in accordance with the invention, said apertures in the iris wherethrough said supporting members are to be inserted are made by means of a focused laser beam.

The proposed method simplifies the technique of the surgical procedure and permits avoiding such complications as injuries to the endothelium and capsule of the eye lens and haemorrhages from the iris that may develop during the perforation of the apertures with the aid of surgical instruments. The method of the present invention permits forming apertures in the periradicular zone of the iris precisely to size.

The invention will be further understood from the following description of an exemplary embodiment thereof with references to the accompanying drawings, wherein:

FIG. 1 depicts an artificial eye lens implantable by the technique in accordance with the present invention;

FIG. 2 - ditto, side elevation;

FIG. 3 shows another embodiment of an artificial eye lens implantable by the technique in accordance with the present invention;

FIG. 4 -- ditto, side elevation;

FIG. 5 illustrates still another embodiment of an artificial eye lens implantable by the technique in accordance with the present invention;

FIG. 6 - ditto, side elevation;

FIG. 7 presents yet another embodiment of an artificial lens implantable by the technique in accordance with the present invention;

Figure 12:
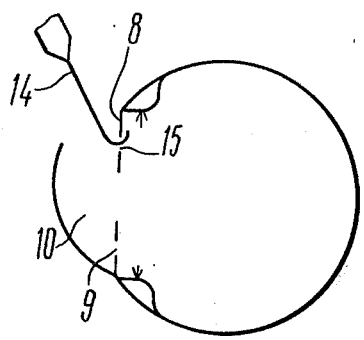
Figure 13:
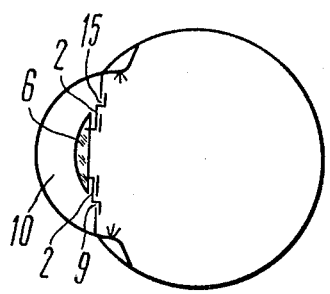
Figure 14:
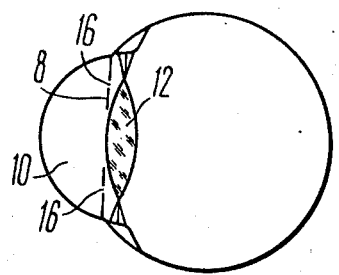
Figure 15:
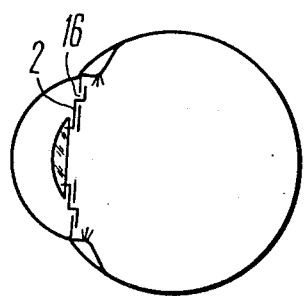

FIG. 12 presents the manipulation of making an aperture in the iris with a surgical instrument;

FIG. 13 illustrates the fixation of supporting members of the artificial eye lens in the apertures formed in the iris;

FIG. 14 shows a sagittal section of the eye with apertures made in the iris by means of a focused laser beam, in accordance with the present invention;

FIG. 15 shows the position of the artificial eye lens in the eye following the fixation of the supporting members thereof in the apertures formed in the iris.

Figure 1:
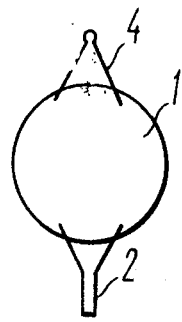
Figure 2:
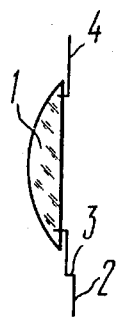
Figure 3:
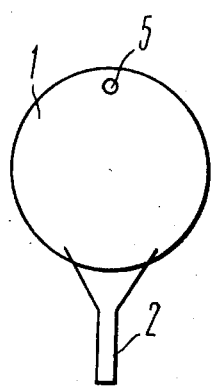
Figure 4:
Figure 5:
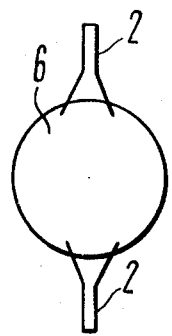
Figure 6:
Figure 7:
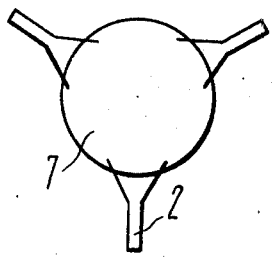

Referring now to the drawings, an artificial eye lens, which may be fixed in the eye by the present method, is an optic lens 1 (FIG. 1) provided with a supporting 2 intended for being passed through an aperture in the periradicular zone of the iris. The supporting member 2 has a step-like bend 3 (FIG. 2) serving as a bearing upon the iris. The optic lens 1 has one supporting member 2, and opposite to the supporting 2 a device is located that serves for passing a surgical suture used for fixing the contralateral side of the optic lens 1 to the periradicular zone of the iris and comprises e.g. a loop 4 (FIGS. 1 and 2) or an aperture 5 (FIGS. 3 and 4). The optic lens however, may be provided with two supporting members 2, as an optic lens 6 (FIGS. 5 and 6), or with three supporting members 2, as an optic lens 7 (FIG. 7). In the latter cases no devices for passing the surgical sutures are needed.

The method of fixation of an artificial eye lens formed as an optic lens 1 (FIGS. 1 and 3) is realized, in accordance with the invention, in the following way.

Figure 8:
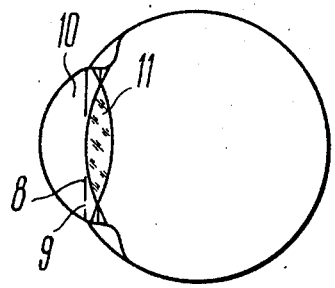
FIG. 8 depicts a sagittal section of the eye with an aperture made in the iris by means of a focused laser beam, in accordance with the present invention.

One aperture 9 is made in the periradicular zone of iris 8 (FIG. 8) intended for passing the supporting member of the artificial eye lens therethrough. The aperture 9 is made with the aid of a focused laser beam. The power of the laser beam may be varied from 0.5 W to 2.0 W; the exposure from 0.05 sec. to 1.0 sec; the diameter of the beam in the focal plane from 50 to 100 micron, and the number of applications from 1 to 100.

Figure 9:
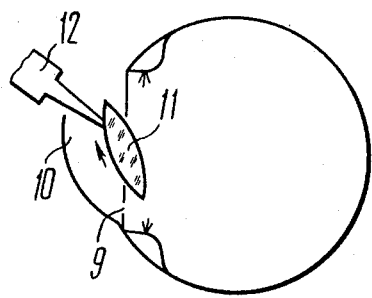
FIG. 9 illustrates the removal of an opacified eye lens.
Figure 10:
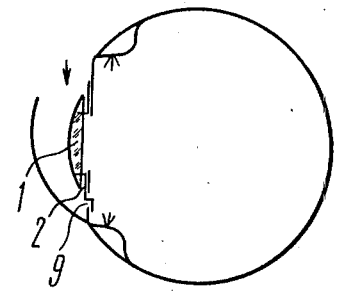
FIG. 10 shows the implantation of an artificial lens.
Figure 11:
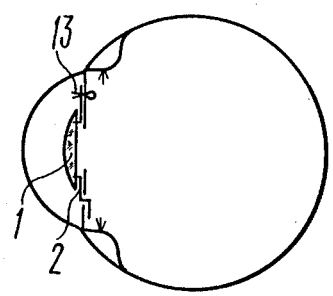
FIG. 11 shows the position of an implanted artificial eye lens in the eye.

Following the above procedure, anterior chamber 10 of the eye is incised along the limbus on the side contralateral to the aperture 9, and opacified eye lens 11 is removed with the aid of a known device, e.g. a cryoextractor 12 (FIG. 9). The artificial eye lens comprising the optic lens 1 (FIG. 10) is introduced into the anterior chamber 10, and the supporting member 2 is fixed in said aperture 9. The optic lens 1 is sutured to the periradicular portion of the iris on the side contralateral to the supporting member 2 by applying a surgical suture 13 (FIG. 11), the eyeball incision being thereafter closed by suturing.

While fixing the optic lens 6 (FIG. 5) or the optic lens 7 (FIG. 7) that are provided with two or three supporting members 2, as well as prior to incising the anterior chamber 10 (FIG. 8) of the eyeball, one aperture 9 is made in the periradicular zone of the iris for the supporting member of the artificial eye lens to be passed therethrough. The aperture 9 is perforated with the aid of a focused laser beam as described above. The anterior chamber 10 of the eyeball is incised along the limbus on the side contralateral to the aperture 9, and the opacified eye lens 11 is removed from the anterior chamber 10, as shown in FIG. 9. Thereafter, employing a surgical technique, e.g. with the aid of a knife-needle 14 (FIG. 12), one or several apertures 15 are perforated in the periradicular zone of the iris 8, the number of said apertures corresponding to that of supporting members of the artificial eye lens used. Upon completing this stage, an artificial eye lens comprising e.g. the optic lens 6 (FIG. 13) with two supporting members 2 is introduced into the anterior chamber 10. The supporting members 2 are fixed in the apertures 9 and 15, and the incision in the eyeball is closed by suturing.

Perforating the apertures 15 with the aid of surgical instruments permits locating said apertures 15 precisely in conformity with the location of the supporting members 2 of the artificial eye lens. However, using a focused laser beam permits applying several apertures 16 at a time (FIG. 14) prior to incising the anterior chamber 10, the number of said apertures 16 in the iris 8 being equal to that of the supporting members of the artificial eye lens to be implanted. Thereafter, the anterior chamber 10 is incised, the opacified eye lens 12 removed, the artificial eye lens fixed by inserting the supporting members 2 thereof (FIG. 5) into the apertures 16, and the eyeball incision closed by suturing.

What is claimed is:

1. A surgical method of fixing an artificial eye lens formed as an optic lens provided with one supporting member with a step-like bend intended to be inserted through an aperture in the periradicular zone of the iris, and a device for applying a surgical suture thereto, comprising the following steps: perforating by means of a focused laser beam one said aperture in the periradicular zone of the iris intended for passing therethrough said supporting member; incising the anterior chamber of the eye on the side contralateral to said aperture; removing the opacified eye lens; implanting an artificial eye lens and fixing said supporting member thereof in said aperture; passing a surgical suture through said device for applying surgical sutures and through the iris for achieving additional fixation of said optic lens to the periradicular zone of the iris; and applying surgical sutures to the eyeball incision.

2. A surgical method of fixing an artificial eye lens formed as an optic lens provided with at least two supporting members with step-like bends intended for being inserted through apertures in the periradicular zone of the iris, comprising the following steps: perforating by means of a focused laser beam one said aperture in the periradicular zone of the iris intended for the insertion therethrough of said supporting member; incising the anterior chamber of the eye on the side contralateral to said aperture; perforating with the aid of surgical instruments apertures to accommodate the rest of the said supporting members; removing the opacified eye lens; implanting an artificial eye lens and fixing said supporting members thereof in said apertures; and applying surgical sutures to the eyeball incision.

3. A surgical method of fixing an artificial eye lens formed as an optic lens provided with at least two supporting members with step-like bends intended for being inserted through apertures in the periradicular zone of the iris, comprising the following steps: perforating by means of a focused laser said apertures in the periradicular zone of the iris intended for the insertion therethrough of said supporting members; incising the anterior chamber of the eyeball; removing the opacified eye lens; implanting an artificial eye lens and fixing said supporting members thereof in said apertures in the periradicular zone of the iris; and applying surgical sutures to the eyeball incision.

* * * * *